(12) United States Patent
Laskin et al.

(10) Patent No.: US 8,927,463 B2
(45) Date of Patent: Jan. 6, 2015

(54) SENSITIVE HIGH THROUGHPUT METHOD FOR DNA DAMAGE AND REPAIR

(71) Applicants: Jeffrey D. Laskin, Piscataway, NJ (US); Diane E. Heck, Rumson, NJ (US); Karma C. Fussell, Garland, TX (US)

(72) Inventors: Jeffrey D. Laskin, Piscataway, NJ (US); Diane E. Heck, Rumson, NJ (US); Karma C. Fussell, Garland, TX (US)

( * ) Notice: Subject to any disclaimer, the term of this patent is extended or adjusted under 35 U.S.C. 154(b) by 0 days.

(21) Appl. No.: 13/860,790

(22) Filed: Apr. 11, 2013

(65) Prior Publication Data

US 2013/0274130 A1 Oct. 17, 2013

(51) Int. Cl.
- C40B 30/04 (2006.01)
- G01N 33/50 (2006.01)
- G01N 33/53 (2006.01)
- G01N 33/52 (2006.01)

(52) U.S. Cl.
CPC ........ *G01N 33/5017* (2013.01); *G01N 33/5308* (2013.01); *G01N 33/5011* (2013.01); *G01N 33/5014* (2013.01); *G01N 33/52* (2013.01)
USPC .......................................................... 506/9

(58) Field of Classification Search
None
See application file for complete search history.

(56) References Cited

U.S. PATENT DOCUMENTS

| | | | |
|---|---|---|---|
| 4,407,942 A | 10/1983 | Birnboim | 435/6.16 |
| 5,863,753 A | 1/1999 | Haugland et al. | 435/34 |

OTHER PUBLICATIONS

Bissonnette et al. (2008) "Real-time Fluorescence-based Detection of Furanocoumarin Photoadducts of DNA" Phytochemical Analysis 19:342-347.*
Moreno-Villanueva et al. (2009) "A modified and automated version of the 'Fluorimetric Detection of Alkaline DNA Unwinding' method to quantify formation and repair of DNA strand breaks" BMC Biotechnology 9:39.*
Bond et al. (1970) "Characteristics of Growth Inhibition of *Lactobacillus casei* by 4-Nitroquinoline-n-Oxide" Applied Microbiology 20(4): 536-538.*
Gurova (2009) "New hopes from old drugs: revisiting DNA-binding small molecules as anticancer agents" Future Oncol 5(10):1685.*
Batel et al. "A Microplate Assay for DNA Damage Determination (*Fast Micromethod*) in Cell Suspensions and Solid Tissues" Analytical Biochemistry 1999 270:195-200.
Kailasam, S. and Rogers, K.R. "A Fluorescence-based Screening Assay for Dna Damage Induced by Genotoxic Industrial Chemicals" Chemosphere 2007 66:165-171.
Rogers, K.R. and Apostol, A. "Detection of Low Dose Radiation Induced DNA Damage Using Temperature Differential Fluorescence Assay" Analytical Chemistry 1999 71(19):4423-4426.
Singer et al. "Characterization of PicoGreen Reagent and Development of a Fluorescence-Based Solution Assay for Double-Stranded DNA Quantitation" Analytical Biochemistry 1997 249:228-238.
International Search Report from ITS/SE12/00090, Sep. 28, 2012, PCT.

* cited by examiner

*Primary Examiner* — Tracy Vivlemore
*Assistant Examiner* — Karen S Weiler
(74) *Attorney, Agent, or Firm* — Licata & Tyrrell P.C.

(57) ABSTRACT

A high throughput method and apparatus for rapidly screening a plurality of genotoxicants to determine the degree and type of genotoxicity are provided.

16 Claims, 5 Drawing Sheets

FIG. 5

SENSITIVE HIGH THROUGHPUT METHOD FOR DNA DAMAGE AND REPAIR

This invention was made with government support under U54AR055073 awarded by the National Institutes of Health. The government has certain rights in the invention.

This patent application claims the benefit of priority from Swedish Patent Application No. SE 1250380-1, filed Apr. 16, 2012, the teachings of which are herein incorporated by reference in their entirety.

FIELD OF THE INVENTION

A method for high throughput screening of genotoxicants is provided. The method involves exposure of DNA to toxicants, addition of an appropriate dye that specifically detects double-stranded DNA, and determination of the melting characteristics during a temperature gradient. Changes in the melting rate, the temperature at which initial melting occurs, and the initial amount of double-stranded DNA is directly proportional to the extent of DNA damage. The method is suitable for high throughput monitoring of the effect of environmental factors on DNA including toxicants and drug and radiation chemotherapy.

BACKGROUND OF THE INVENTION

By the time Watson and Crick described the structure of DNA in 1953, its loss of structure at high pH or temperature was already well known. The double-helix structure made it obvious that DNA could be unzipped by breaking the hydrogen bonds holding the two helices together; this was the mechanism by which DNA melting occurred. Early work focused on synthetic DNA sequences found that the length of the DNA sequence and percentage of CG base pairing were directly proportional to increases in melting temperature (Tm) or pH. Today, in addition to its uses as a measure of DNA length and % CG content, DNA melting curves are used to elucidate epigenetic modifications (DNA methylation) and to detect single nucleotide polymorphisms (SNPs) in individual genes.

These advances have been possible due to adaptation of cellular DNA replication machinery to synthetic gene amplification by PCR. This technique uses fluorescent dyes to measure increases in DNA concentration during temperature cycling. Once amplification is complete, these dyes enable post-PCR melting curves to verify Tm as a test of amplification specificity. Because DNA melts within a narrow temperature range (a few ° C.), melting curve acquisition requires the imaging and temperature control capabilities provided by a real-time thermocycler.

Such DNA melting curves are possible because these dyes fluoresce preferentially when intercalated into double-stranded, but not single-stranded DNA. As the DNA denatures, the dye is no longer stabilized by the negatively charged DNA backbone and the fluorescence is quenched. This mechanism is common to most DNA-binding dyes; however the degree of double-stranded specificity is a property of each dye. If the melting curve is preceded by amplification, a large amount of specificity is not required as the amplification step reduces any nonspecific binding to levels below the noise threshold. However, if no amplification is performed, then this dye must be very specific for double-stranded DNA (dsDNA) (more than 100-fold over single-stranded DNA (ssDNA) and RNA).

To date, determination of genotoxicity is extremely low throughput. Many current assays measure either bacterial or mammalian cell growth in media treated with potential mutagens. Other cell-based assays take a gene induction-based approach, using reporter assays to measure induction of key DNA damage proteins in mammalian cell lines, such as repair enzymes. However the cellular machinery for fixing DNA double-strand breakage, single-strand breakage, and nucleotide base damage are vastly different, necessitating separate tests. Furthermore, there is cross talk between the pathways mediating signal induction, which can lead to false positive and false negative tests. Attempts to increase throughput of cell-based assays using microtiter plate readers have floundered because ensuring the quality of these assays between plates is difficult. Current in vitro genotoxicity tests, such as comet assays and 8-hydroxy-2-deoxyguanosine production, ignore some forms of DNA damage, like adduct formation and DNA strand cross linking, in favor of others. In the end, multiple assays must be performed and disparate data must be compared. None of these techniques readily lends itself to testing multiple compounds at the same time and the use of compression is vital when testing a library containing millions of compounds.

Three groups have used highly specific dsDNA binding dyes to quantify DNA damage by melting curve analysis (Singer et al. Anal Biochem. 1997 249:228-238; Kailasam et al. Chemosphere 2007 66:165-171; Rogers K R and Apostol A, Anal Chem 1999 71: 4423-4426; Batel et al., Anal. Biochem. 1999 270:195-200). The first measured changes in the rate of dsDNA denaturation at high pH and correlated this to radiation exposure. However this technique requires the entire DNA to be of the same sequence and length and the pH of the buffer to be exactly determined, making it impractical for use as a high-throughput assay. The second group used temperature to denature the radiation-damaged dsDNA. However, their methodology was flawed as they performed measurements after heating the DNA to only three temperatures in a waterbath and required the fluorescence of the DNA binding dye, in this case PicoGreen, be determined immediately, before the DNA could re-anneal. Again, this technique requires the DNA to be of the same sequence and length and does not lend itself to a high-throughput screen. The third group measured loss of fluorescence after successive melting and re-annealation qPCR cycles. This decrease in fluorescence is attributed to the loss of small DNA fragments resulting from radiation damage. While this endpoint assay is the most high-throughput of the three techniques, it still quantifies only DNA strand breakage since it does not measure the entire melting curve, but only the initial value of each cycle. Nor does it accurately quantify DNA strand breakage, since the large DNA fragments formed could still re-anneal (U.S. Pat. No. 4,407,942 10/1983 and U.S. Pat. No. 5,863,753 1/1999).

In light of the foregoing, it would significantly advance the art if a quantitative method for detecting genotoxicity was developed that could simultaneously differentiate between different forms of DNA damage formation. It would be an additional advancement if such an assay could take advantage of high-throughput technological developments such as fluidics automation and dense microtiter formats to produce rapid, accurate results without being labor-intensive. Such a method is disclosed herein.

SUMMARY OF THE INVENTION

This invention overcomes the drawbacks of previous genotoxicity assays by providing a high-throughput screening assay for DNA damaging agents in which the degree and type of DNA damage is simultaneously detected.

A prime objective of the invention is to provide an in vitro fluorometric or spectrophotometric DNA melting assay to identify and quantify many forms of genotoxicity. In one embodiment, this assay comprises a dsDNA specific dye, a reference dye, dsDNA, and the experimental system, wherein the dsDNA is exposed to the experimental genotoxicants and the dsDNA and reference dyes. The samples are sealed and loaded into a real-time thermocycler to analyze the melting curves. Curves from experimental samples are compared to those from control samples in three parameters. Potential means to detect genotoxicity include: 1) initial fluorescence, since double-strand breaks increase the number of DNA molecules, while DNA intercalating agents compete with the dye for DNA binding, 2) initial melting rate, since strand breakage and monofunctional alkylation increases the amount of early stage DNA melting, while thymine crosslinking and bifunctional alkylation decrease the initial melting rate, and 3) the temperature at which initial melting occurs (Ti), since strand-breakage and monofunctional alkylation will decrease Ti, while bifunctional alkylation, DNA strand cross-linking, and intercalation will increase Ti. Genotoxicants may have more than one mechanism of action; for instance, cisplatin is a chemotherapeutic that acts as both an intercalating agent and a bifunctional alkylating agent. This assay is suitable for any Society for Biomolecular Screening standardized microtiter plate and may be easily adapted to higher density formats including microfluidics- and array-based systems.

Thus, an aspect of the present invention is to provide a high-throughput method to identify anti-neoplastic compounds, antiproliferative compounds and antimicrobial compounds.

Another aspect of the present invention is to provide a high-throughput method to identify potential mutagens in pharmaceutical drug compound libraries.

Another aspect of the present invention is to provide a method to quantify the genotoxicity resulting directly or indirectly from metabolism of any compound.

Another aspect of the present invention is to provide a method to measure the genotoxic activity downstream of any chemical, biologic, protein, enzyme, or signaling molecule.

Another aspect of the present invention is to provide a method to identify genotoxicity resulting from alterations to cellular machinery, especially DNA repair machinery.

Another aspect of the present invention is to provide a method to quantify genetic (single nucleotide polymorphisms, mutations, etc.) or epigenetic changes in DNA (supercoiling, methylation, etc.).

DETAILED DESCRIPTION OF THE INVENTION

The present invention provides a method to screen for compounds that modulate DNA melting-curves. Identification of such compounds has significance for both the pharmaceutical and medical industries. Compounds that cause genotoxicity are mutagenic and carcinogenic and their therapeutic use should be avoided, except for use in specific diseases such as cancer. Conversely, compounds with potential for either prevention or stimulation of repair have several uses, including as cancer chemopreventatives and adjuvant therapeutics. Similarly, the ability to detect DNA damage reliably and quickly is useful in certain diagnostic procedures; such as to detect precancerous DNA damage, genotoxicity as a result of a particular therapy, or DNA integrity prior to instigation of a therapy.

Methods to reliably determine both the type(s) of DNA damage and the degree of the genotoxicity in a high-throughput fashion have not been available until the present invention.

For the purposes of describing this invention the following terms will be helpful and have the following meanings:

Definitions

The term "specific structure" as used herein refers to any nucleic acid structure not recognized as double-stranded DNA.

The term "DNA" refers to deoxyribonucleic acid. It will be understood by those of skill in the art that where manipulations are described herein that relate to DNA, they will also apply to other specific structures of DNA or RNA. dsDNA refers to double strand DNA. ssDNA refers to single strand DNA.

As used herein, the term "intercalate" refers to insertion between the layers of the DNA base pair ladder.

The term "mutations" refers to alterations in the sequence of a wild-type nucleic acid sequence or changes in the sequence of a peptide. Such mutations may be point mutations such as transitions or transversions. The mutations may be deletions, insertions, or duplications.

As used herein, "DNA damage" or "specific DNA damage" refers to DNA that is not normally present in an intact cell under physiological conditions during interphase. DNA backbone strand breaks, for instance, are not produced normally in an interphase cell. Strand breaks are produced, however, by certain drugs and ultraviolet or ionizing irradiation. For the purposes of this invention all backbone disruptions are considered strand breaks. Other DNA damage may include the covalent attachment of chemical moieties to DNA, base-pair intercalation, or a combination of modes of DNA damage.

The term "genotoxicant" as used herein refers to a genotoxic compound, chemical, enzymes such as DNAse or a biological misregulation such as failed DNA repair or a biological process, wherein the genotoxicant results from a chemical, biological, or physical process. The source of the genotoxicant may vary greatly depending on the investigators area of interest.

The term "genotoxicity" as used herein refers to the formation of DNA damage or the disruption of normal nucleic acid structure, which can result in DNA mutations.

As used herein, the term "melting-curve" refers to the denaturation or annealation of DNA in response to changes in temperature, pH, ionic strength, urea concentration, or organic content.

As used herein, the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation ($Mg^{2+}$, $Ca^{2+}$); preferably about 150 mM NaCl or KCl, pH 7.2-7.6, 5 mM divalent cation, and often include 0.01-1.0 percent nonspecific protein (e.g. BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods.

The term "microtiter plate" as used herein refers to the physical linkage of at least two vessels. More often a microtiter plate comprises the physical linkage of several vessels, such as 96 vessels in an array format. A microtiter plate may have less than, or more than 96 wells.

The term "low-density format" as used herein refers to the use of individual test tubes or a 6-, 12-, 24- or 48-well microtiter plate.

The term "high-density format" as used herein refers to the use of a 96-, 384- or 1536-well microtiter plate. An ultra high density format on a microarray or microfluidics chip means 10.000 or 100.000 or more reaction vessels per array.

Real-Time DNA Melting Assay

Components of this assay include 1) a reaction vessel free from DNase and RNase, 2) a dsDNA-specific dye, 3) a reference dye 4) dsDNA, and 5) the genotoxicant(s). In this nonlimiting example, the dsDNA-specific dye is PicoGreen, the reference dye is ROX, the dsDNA comes from calf-thymus and has been modified to demonstrate different known types of DNA damage. As the sample is heated in the real-time thermocycler, the dsDNA melts becoming single-stranded. Single-stranded DNA no longer supports PicoGreen fluorescence, thus the relative amount of PicoGreen to ROX fluorescence declines proportionally to the loss of DNA base-pairing. As will be understood by the skilled artisan upon reading this disclosure, alternative fluorometric dyes or spectrophotometric dyes can be used in the method of the present invention.

The DNase and RNase free reaction vessel that can be used for this assay includes a container capable of holding any volume made of conventional or unconventional materials, including (but not limited to) polystyrene, polyvinyl chloride, polycarbonate, metal, or glass. The surface of the reaction vessels can be treated, derivatized, or coated. Often, for high throughput assays, the vessels are comprised of microtiter plates. In one embodiment, the dsDNA is derivatized to the wells of a microtiter PCR plate or an ultra-high throughput chip. In another embodiment, PCR plates are cell culture treated, to ensure cellular adherence.

A quantity of dsDNA is then added to any empty reaction vessel. The dsDNA may be from any source, whether synthetic, bacterial, viral, plant, or animal; and may be of any sequence or length. The dsDNA may be previously nicked, cut, amplified, or processed by any procedure known to a practitioner skilled in the art.

The DNA is then treated with the genotoxicant, which may be used independently, or may be administered jointly with any treatment system, including (but not limited to) any metabolizing enzyme, cell fraction, cofactor, or organism that alters, enhances, or ameliorates DNA damage potential. Treatment with the genotoxicant may occur for any length of time before, during, or after addition of fluorescent dye(s).

Following treatment with the genotoxicant, a cocktail of dsDNA-specific and reference dyes is added to the reaction vessel. Any indicator with selectivity for dsDNA may be used with or without a reference indicator for normalization. Once dyes are added, the reaction vessel is sealed and subjected to melting curve analysis.

Melting curve analysis is typically performed in a real-time thermocycling instrument. This apparatus has the advantages of exquisitely sensitive sample temperature control as well as a fluorescence detection system. However, a practitioner skilled in the art could use any appropriate system to perform the DNA melting analysis. The output of such instruments is the measured output from one or more fluorescence transitions and the temperature at which that fluorescence was determined.

Figure 1:
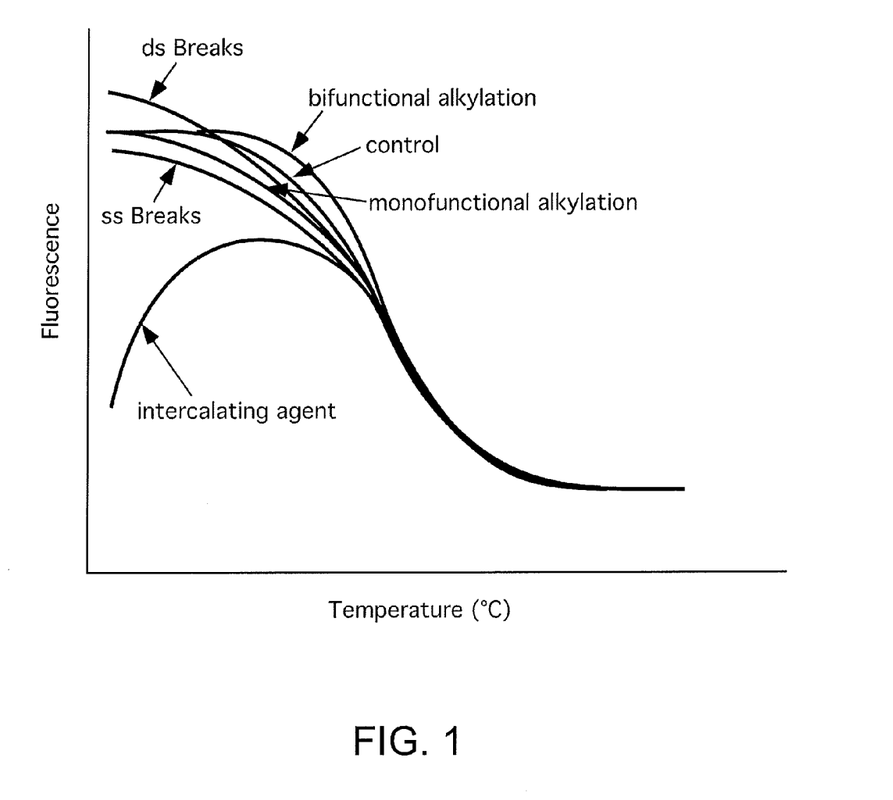
FIG. 1 shows a schematic drawing of the melting curves of DNA with representative types of DNA damage.

In one embodiment, the raw dsDNA-specific fluorescence is normalized to the corresponding reference fluorescence at each temperature point to correct for decreased dye fluorescence resulting directly from the increasing solution temperature. This normalized fluorescence is then graphed as a function of temperature to produce the melting curve. Initial fluorescence from this curve is used to determine the extent of double-strand breakage. The first derivative of this melting curve is then plotted and used to determine both the initial melting temperature and the melting rate across the entire temperature gradient. Comparison of these data with negative control data (no DNA damage) and positive control data (sample known genotoxicant) co-analyzed on the same plate reveals the type and extent of DNA damage. A schematic representation of the typical melting curves is shown in FIG. 1 wherein, with increasing pH, salinity, or temperature, DNA dissociation increases resulting in a decrease in relative fluorescence. The type and quantity of DNA damage substantially alters the characteristics of this melting curve, such that this assay can be used to qualitatively and quantitatively describe the genotoxic potential of unknown compounds.

The method according to this invention may, for example, be used in the detection of DNA damage to qualify or disqualify DNA for further analysis, including, but not limited to: (a) genetic or genomic analyses of a single-cell or a population of cells; (b) gene or genome sequencing, including, but not limited to, targeted sequencing, exome sequencing, whole genome sequencing, NextGen sequencing, and ChIP-sequencing; (c) genotyping, including, but not limited to, detection of single-nucleotide polymorphisms or whole genome genotyping; (d) gene expression analysis, including, but not limited to, real-time or quantitative PCR, microfluidics-, chip-, or array-based high-throughput expression analysis; and (e) copy number analysis, including, but not limited to, determination of the copy number variation between individual cells or organisms.

The method according to the present invention can further be used in the detection of DNA damage to qualify or disqualify DNA for diagnostic testing applications, including, but not limited to: (a) DNA arising from whole-blood, serum, or any other biological source; and (b) free-floating DNA.

The method according to any of the described embodiments can be used for identifying genotoxicants to develop a method of treating a condition, disease or disorder in humans or animals by developing a DNA binding compound comprising: (a) screening compounds according to the assay recited in this application; (b) selecting those compounds which show the greatest degree of effects on DNA melting; (c) formulating a pharmaceutical composition comprising one or more of any of these compounds; and (d) administering the pharmaceutical composition to a subject in need of such treatment.

The compounds mentioned in step (a) can be the same genotoxic compounds as mentioned in the beginning of the paragraph or they can be different because they are therapeutic.

An apparatus to be used according to the methods described in this application for screening a plurality of genotoxicants may comprise: (a) a plurality of test wells into which a volume of dsDNA can be added, and (b) equipment for monitoring DNA-melting, including, but not limited to, equipment used to detect DNA using native absorption, or fluorescent or spectrophotometric DNA dyes; and (c) equipment for analyzing melting curves, preferably a thermocycler. The test wells of the apparatus may further comprises a container capable of holding any volume made of conventional or unconventional materials, including, but not limited to, polystyrene, polyvinyl chloride, polycarbonate, metal or glass, and wherein the test wells optionally are treated, derivatized or coated.

The following nonlimiting example is provided to further illustrate the present invention.

EXAMPLE

Several pharmacologically important genotoxicants are known to exist. Many of these genotoxicants are used as antineoplastic and antiproliferative therapeutics, and are prescribed as chemotherapeutics and antibiotics. However, not all chemotherapeutic and antibiotic treatments exert their effects through a genotoxic mechanism. Thus, testing a genotoxicity assay against known antineoplastic and antiproliferative pharmacologic agents represents a useful proof-of-concept.

The ability to detect DNA-damaging agents was first examined under conditions under which only the pharmaceutical agent was allowed to interact with the dsDNA. FIGS. 2-5 show examples of the effects of chemicals that modify DNA on DNA melting profiles.

Figure 2:
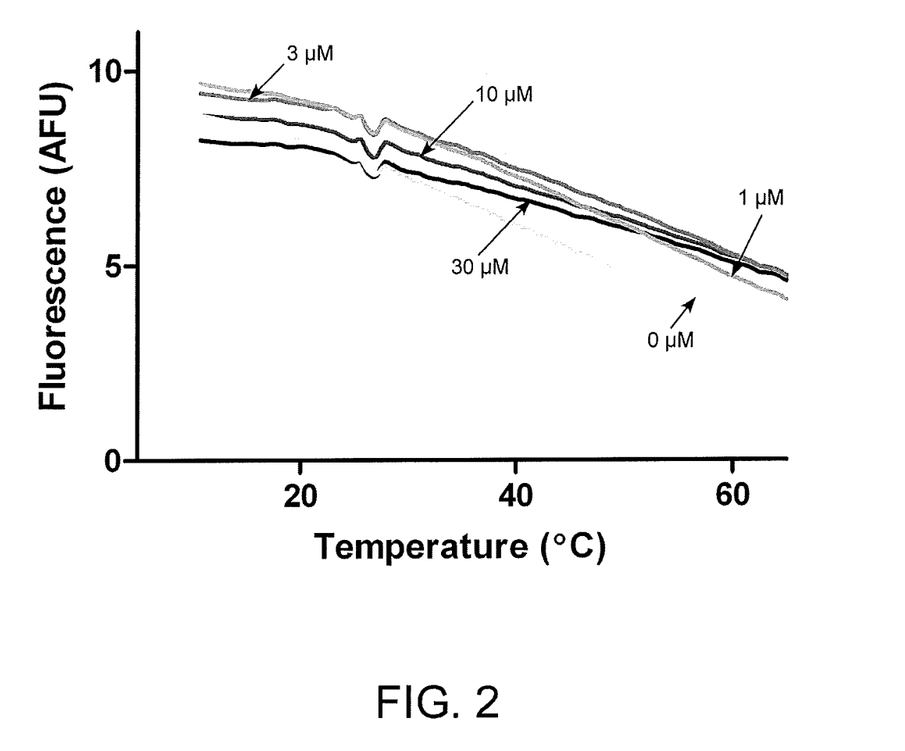
FIG. 2 shows the effect of increasing concentrations of phenanthrenequinone on DNA melting curves.

FIG. 2 shows the effect of phenanthrenequinone on DNA melting curves. dsDNA (1,000 ng/ml), treated with increasing concentrations of the alkylating agent phenanthrenequinone, was incubated with PicoGreen and the rhodamine ROX reference dye. Samples were analyzed using an ABI 7300 real time thermocycler over a temperature range of 4° C. to 99° C. Data is presented as PicoGreen fluorescence normalized to ROX. These data show that increasing dsDNA alkylation causes an increase in the initial melting temperature. This means that increases in initial melting temperature compared to control indicates double-stranded DNA alkylation.

Figure 3:
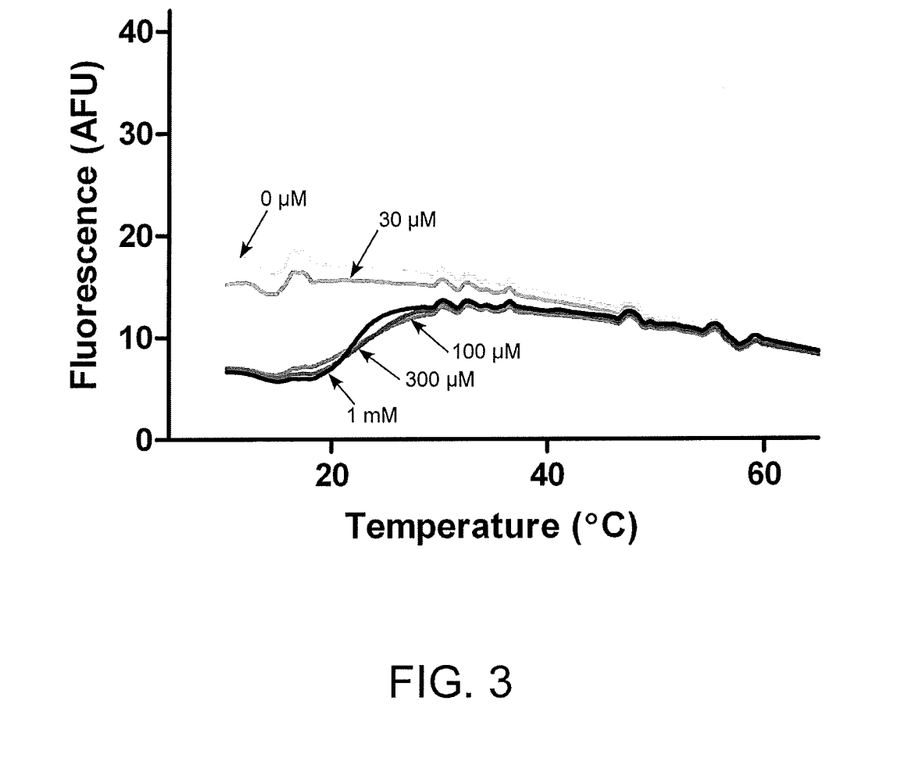
FIG. 3 shows the effect of increasing concentrations of hexestrol on DNA melting curves.

FIG. 3 shows the effect of hexestrol on DNA melting curves. dsDNA (1,000 ng/ml), treated with increasing concentrations of the intercalating agent hexestrol, was incubated with PicoGreen and the rhodamine ROX reference dye. Samples were analyzed using an ABI 7300 real time thermocycler over a temperature range of 4° C. to 99° C. Data is presented as PicoGreen fluorescence normalized to ROX. These data show that increasing dsDNA intercalation causes a decrease in the initial melting temperature. These data show that increasing dsDNA intercalation causes a decrease in fluorescence. This means that there is a decrease in the initial melting temperature of the dsDNA and indicates the presence of an intercalating agent.

Figure 4:
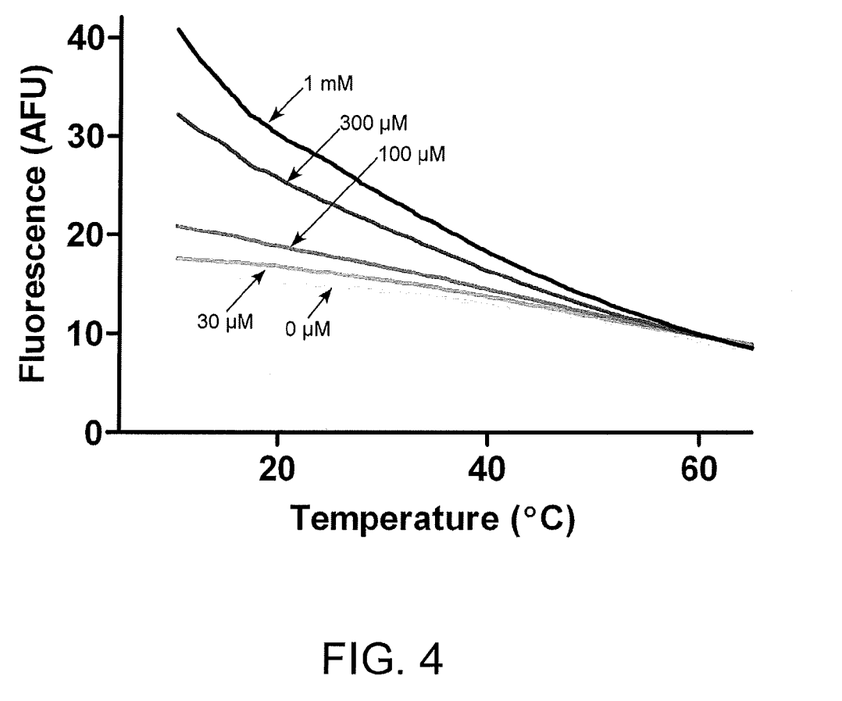
FIG. 4 shows the effect of increasing concentrations of 2-hydroxyestradiol on DNA melting curves.

FIG. 4 shows the effect of 2-hydroxyestradiol on DNA melting curves. dsDNA (1,000 ng/ml), treated with increasing concentrations of the DNA strand scission agent 2-hydroxyestradiol, was incubated with PicoGreen and the rhodamine ROX reference dye. Samples were analyzed over a temperature range of 4° C. to 99° C. using an ABI 7300 real time thermocycler. Data is presented as PicoGreen fluorescence normalized to ROX. These data show that increasing dsDNA scission causes an increase in initial melting slope due to single strand breakages. When single strand breaks are in close proximity, double strand breaks can result. This is shown above as an increase in initial fluorescence.

Figure 5:
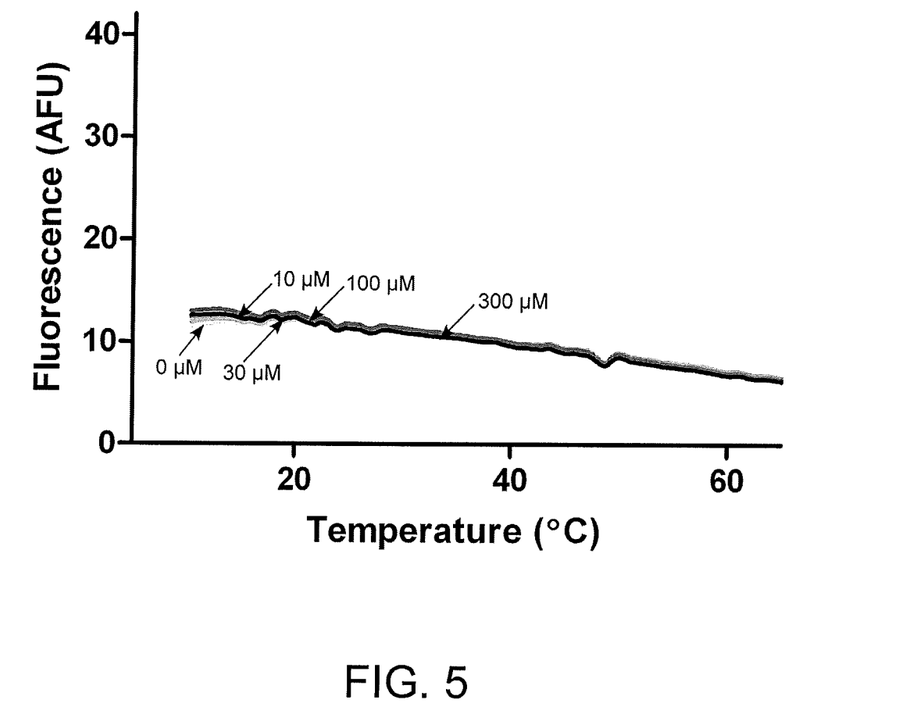
FIG. 5 shows the lack of effect of increasing concentrations of camptothecin on DNA melting curves.

FIG. 5 shows the effect of camptothecin on DNA melting curves. dsDNA (1,000 ng/ml) was treated with non-genotoxic concentrations of camptothecin and incubated with PicoGreen and the rhodamine ROX reference dye. Samples were analyzed using an ABI 7300 real time thermocycler over a temperature range of 4° C. to 99° C. Data is presented as PicoGreen fluorescence normalized to ROX. These data show that the nongenotoxic camptothecin does not alter DNA melting.

The present invention can also be applied as a screen for novel anti-neoplastic, anti-proliferative, and antimicrobial therapeutics. These compounds often exert their anti-neoplastic, anti-proliferative, and antimicrobial properties via a genotoxic mode of action. The present invention can be used as a high-throughput screen to identify potential novel anti-neoplastic, anti-proliferative, and antimicrobial therapies from multimillion compound drug libraries. While the ability to damage DNA might be an important feature for these special classes of drugs, mutagenicity is generally considered an undesirable characteristic in a drug candidate. Mutagens often advance into expensive preclinical testing before this characteristic is identified and the drug is removed from candidacy; therefore, it is extremely desirable to identify poor lead compounds earlier in the drug development process. The present invention can be used to screen entire compound libraries to identify potential mutagens or compounds that are metabolized to mutagens before they enter preclinical development. In the latter case, compounds can be placed into the assay after they have been treated with enzymes that can cause them to be metabolized. For example, compounds can first be treated with microsomal fractions that are known to mediate metabolism or cytochrome P450 enzymes. The compounds can then be added to the assays to assess DNA damage. In one embodiment of the high throughput screen, the enzymes mediating metabolism can be added directly to the reaction vessels simultaneously with the DNA which can then be assayed for its fluorescence characteristics.

The present invention can be extended to any DNA source, including that which is isolated from cells or tissues. Therefore, it would be routine for someone practiced in the art to extend the present invention to the detection of DNA damage resulting from the treatment of these cells and tissues. Thus, this assay can be used to detect genotoxicity resulting from alterations to cellular machinery, or any such activity downstream of any chemical, biologic, protein, enzyme, or signaling molecule, or finally resulting from any genetic or epigenetic changes in the DNA.

What is claimed is:

1. A high throughput method for rapidly screening a plurality of genotoxicants to simultaneously detect degree and type of DNA damage comprising the steps of:
   (a) adding a volume of dsDNA to test wells;
   (b) adding a volume of genotoxicants to be evaluated to the test wells;
   (c) adding dsDNA specific dye and reference dye to the test wells;
   (d) monitoring a detectable signal, using fluorescent or spectrophotometric technique, emitted from test wells while melting the DNA; and
   (e) analyzing melting curves for the
      (i) initial detectable signal,
      (ii) initial melting rate and
      (iii) temperature, pH or salinity level of initial melting, and comparing these parameters to those of controls so that degree and type of DNA damage caused by the genotoxicants can be simultaneously detected.

2. The method of claim 1, wherein the technique in step (d) is a fluorescent technique.

3. The method of claim 2 wherein a thermocycler is used to melt the DNA and/or record the fluorescent signal.

4. The method of claim 1, wherein the addition of the genotoxicants in step b) is made jointly with another treatment system, which treatment system can be any metabolizing enzyme, cell fraction, cofactor, organism that alters, enhances or ameliorates DNA damage potential, and/or wherein genotoxicant exposure includes the use of epigenetic regulators or modulators.

5. The method of claim 1, wherein the genotoxicants are
   (a) one or more chemical products, either synthetic or natural;
   (b) a biologic, whether protein, lipid, carbohydrate, nucleic acid, or a combination of these;
   (c) a physical or chemical process;
   (d) a library of genotoxic compounds; or
or any combination of (a), (b), (c) and (d).

6. The method of claim 1, wherein at least one of the steps is performed robotically.

7. The method of claim 1, wherein the genotoxicity is a direct or indirect result of a biologic change or process or synthetic manipulation.

8. The method of claim 1 performed in a low- or high-density format comprising single tubes, microtiter plates, chips or microfluidics arrays.

9. The method of claim 1 further comprising DNA amplification preceding any of steps (a) through (d) or following step (e).

10. The method of claim 1, wherein the dsDNA is cellular, biologic, or synthetic DNA, with or without lysis or purification steps.

11. The method of claim 1 wherein the dsDNA is isolated from cells or tissues exposed or unexposed to genotoxicants.

12. The method of claim 1 wherein the degree and type of DNA damage detected is indicative of the genotoxicant having antineoplastic, antiproliferative and/or antimicrobial activities.

13. The method of claim 1 wherein the genotoxicants screened are found in food, water, air, pesticides, consumer products or any other residential, agricultural, environmental or industrial application.

14. The method of claim 1 wherein the DNA damage is further analyzed by:
   (a) genetic or genomic analyses of a single-cell or a population of cells;
   (b) gene or genome sequencing;
   (c) genotyping;
   (d) gene expression analysis; or
   (e) copy number analysis.

15. A method of identifying a DNA binding compound comprising:
   (a) screening compounds according to the method of claim 1; and
   (b) identifying those compounds which show increased initial melting rate, increased melting of DNA from temperature, pH or salinity, decreased initial detectable signal and/or increased initial fluorescence signal as compared to controls, indicative of DNA binding capabilities of the compounds.

16. The method of claim 15 wherein the identified DNA binding compound is formulated into a pharmaceutical composition to treat a condition, disease or disorder in a human or animal in need thereof.

* * * * *